US007897085B2

(12) United States Patent
Ancorotti et al.

(10) Patent No.: US 7,897,085 B2
(45) Date of Patent: Mar. 1, 2011

(54) PROCESS FOR THE MANUFACTURE OF MULTICOLOR POURED COSMETICS

(75) Inventors: Renato Ancorotti, Milan (IT); Luigi Gandini, Milan (IT)

(73) Assignee: Chromavis S.p.A., Milan (IT)

( * ) Notice: Subject to any disclaimer, the term of this patent is extended or adjusted under 35 U.S.C. 154(b) by 611 days.

(21) Appl. No.: 11/547,510

(22) PCT Filed: Mar. 29, 2005

(86) PCT No.: PCT/IB2005/000785
§ 371 (c)(1),
(2), (4) Date: Nov. 28, 2006

(87) PCT Pub. No.: WO2005/094759
PCT Pub. Date: Oct. 13, 2005

(65) Prior Publication Data
US 2008/0277827 A1    Nov. 13, 2008

(30) Foreign Application Priority Data
Apr. 2, 2004    (IT) .............................. MI2004A0668

(51) Int. Cl.
*B29C 39/12*    (2006.01)
*A61K 8/00*    (2006.01)
(52) U.S. Cl. ........... 264/245; 264/157; 264/255; 424/63; 424/64; 424/424

(58) Field of Classification Search ................... 264/255, 264/245–247, 157–160; 425/803, DIG. 32; 424/401, 63, 64; 132/303
See application file for complete search history.

(56) References Cited

U.S. PATENT DOCUMENTS

| 235,799 A | * | 12/1880 | Naylor ......................... 264/158 |
| 2,425,431 A | | 8/1947 | Le Vangie |
| 4,060,358 A | * | 11/1977 | Fougea ........................... 425/65 |
| 4,938,675 A | * | 7/1990 | Contreras et al. ............. 425/121 |
| 4,952,400 A | * | 8/1990 | Tararuj et al. ................. 424/401 |
| 5,086,791 A | * | 2/1992 | Ferrari .......................... 132/200 |
| 5,407,691 A | * | 4/1995 | Przelomski et al. ........... 426/249 |
| 5,597,300 A | * | 1/1997 | Wohl et al. .................... 431/288 |
| 2002/0041788 A1 | | 4/2002 | Look et al. |

FOREIGN PATENT DOCUMENTS

| FR | 977 194 A | 3/1951 |
| JP | 62 111906 A | 5/1987 |
| JP | 2002 154930 A | 5/2002 |

OTHER PUBLICATIONS

International Search Report of PCT/IB2005/000785, mailed Aug. 26, 2005.

* cited by examiner

*Primary Examiner* — Kat Wyrozebski
*Assistant Examiner* — Scott W Dodds
(74) *Attorney, Agent, or Firm* — Nixon & Vanderhye P.C.

(57) ABSTRACT

The invention relates to a process for preparing a multicoloured poured cosmetic product, particularly a process for obtaining a multicoloured lipstick, gloss or cosmetic product for the eye contour area, as well as the products obtained by means of this process.

13 Claims, 2 Drawing Sheets

PROCESS FOR THE MANUFACTURE OF MULTICOLOR POURED COSMETICS

This application is the US national phase of international application PCT/IB2005/000785, filed 29 Mar. 2005, which designated the U.S. and claims priority of IT MI2004A000668, filed 2 Apr. 2004, the entire contents of each of which are hereby incorporated by reference.

SUMMARY OF THE INVENTION

The present invention relates to a process for preparing a multicoloured poured cosmetic product, particularly a process for obtaining a multicoloured product such as a lipstick, a gloss or cosmetic product intended for the eye contour area.

TECHNICAL BACKGROUND

With "poured cosmetic product" is generally meant lipsticks and glosses, i.e. those products obtained from the solidification of a mixture of waxes, fats and pigments; these products are normally placed by pouring (i.e. pouring) them in suitable containers where they solidify by cooling.

In the field of poured cosmetic products, it is known for example to manufacture multicoloured cosmetic products by simultaneously delivering two substantially fluid cosmetic products into a suitable container by means of a multi-compartment reservoir that is provided with a moulded delivery matrix. The Japanese patent application JP 2003-306412 (TOKIWA Corp.) describes a similar process.

This technique of simultaneously delivering fluid cosmetic products implies a certain mixing between products of different colours, and accordingly the division of the colours making up the final cosmetic is not neat. Furthermore, the technique described in the application in the name of TOKIWA dictates the use of an equipment dedicated to the implementation of this technique.

It is also known to use multicoloured cosmetic products in which at least two cosmetic products having different colours are arranged in the same container, such as to be mutually separated and thereby leaving the user free to choose which colour to use.

The object of the present invention is to provide a multicoloured poured product that does not suffer from the drawbacks of the prior art.

Another object of the present invention is to provide a process for preparing a multicoloured poured cosmetic product that does not require particular and expensive equipment and comprises a few simple operations.

DESCRIPTION OF THE INVENTION

These and other objects are achieved by means of the process for preparing a cosmetic product of the present invention which comprises:
a) arranging a first layer of cosmetic product by pouring a preset amount of said first coloured melted cosmetic product on a plane, within a containment perimeter;
b) after the layer poured in the preceding step has solidified, pouring a preset amount of a second melted cosmetic product of a different colour from the first one within the containment perimeter;
b') optionally repeating step (b) one or more times in order to superimpose other layers of cosmetic products of different colours;
c) removing the containment perimeter, thereby obtaining a multicoloured or "dégradé", multilayered block; and
d) sectioning, according to cutting planes incident to the layers of coloured cosmetic products, the multicoloured or "dégradé", multilayered block in order to obtain multicoloured or "dégradé" sections of the same.

The multicoloured or "dégradé" sections obtained in step (d) are the final product of the process of the present invention. This final product can be inserted in a suitable base and be then optionally pressed. According to the present invention, the term "poured cosmetic" is meant to indicate cosmetic products such as lipsticks and glosses (or lip glosses) as well as blushers and creamy eye-shadows, under-eye circle concealer and compact foundation.

According to the process of the invention, the poured cosmetic product is thus prepared by subsequent solidification of various different coloured layers of the same cosmetic product in the melted state. The starting cosmetic product has a composition known in the art and can be prepared according to the conventional methods.

The "containment perimeter" employed according to the present invention allows to give the poured cosmetic a shape that will be maintained after the same has solidified by cooling.

This containment perimeter is substantially a hollow cylindrical frame suitable to define the poured cosmetic product on the sides thereof. This frame is rested on the plane on which the first layer is poured (step a).

The containment perimeter can be a single hollow cylindrical frame of a sufficient height to contain all the layers of poured products requiring to be superimposed.

Alternatively, the containment perimeter can consist of two or more hollow cylindrical elements, each having the same height as a layer of poured cosmetic product to be sequentially superimposed upon steps (b) and (b').

The plane on which the cosmetic product is poured in step (a) can be either integral with the containment perimeter or disjointed therefrom. According to a preferred aspect of the invention, the plane is a flat surface, such as a table, board, etc., the containment perimeter such as described above being laid thereon.

The shape of the multicoloured, multilayered block will be defined by the shape of the containment perimeter, which is preferably square or rectangular; other shapes, such as round or oval, can be however provided.

Said containment perimeter can be made of any material consistent with the poured cosmetic product, such as metal, glass, or plastic or silicone materials.

DESCRIPTION OF THE FIGURES

The annexed figures illustrate several embodiments of the invention, in particular.

DETAILED DESCRIPTION OF THE INVENTION

Figure 1:
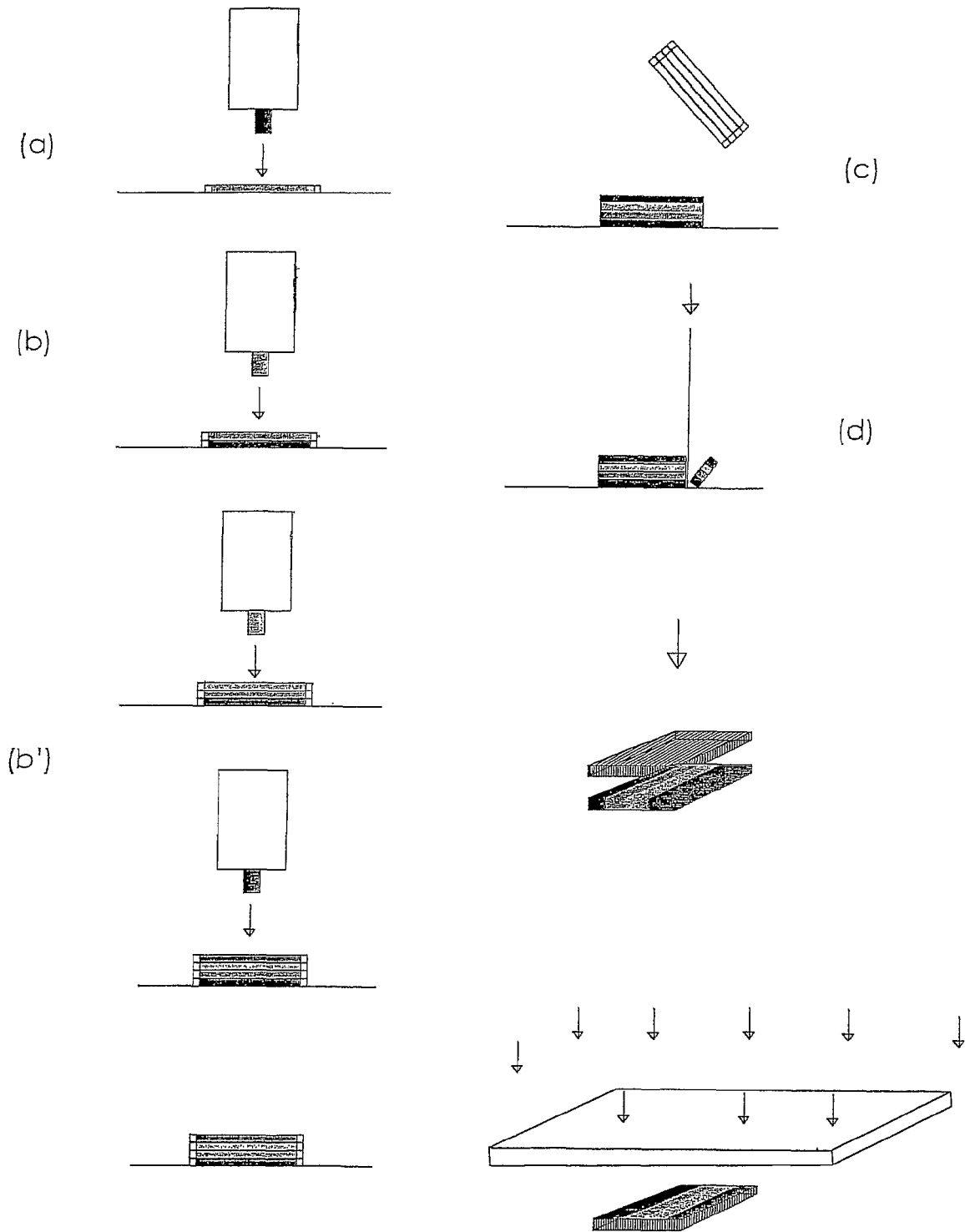
FIG. 1 schematically illustrates the steps (a) to (d) of the process, in which the containment perimeter is formed by four rectangular-based hollow cylindrical elements that are superimposed upon processing; the phases 8 and 9 illustrate the steps in which the finished product is inserted in the base and pressed.
Figure 2:
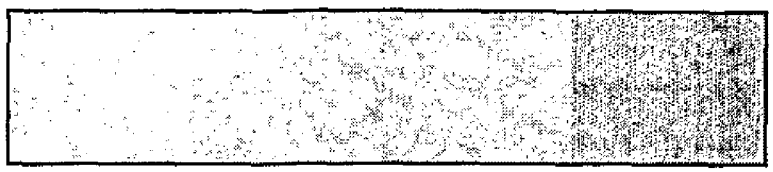
FIG. 2 illustrates several possible multicoloured sections that are obtained by cutting the multilayered solid block.
Figure 2:
Figure 2:
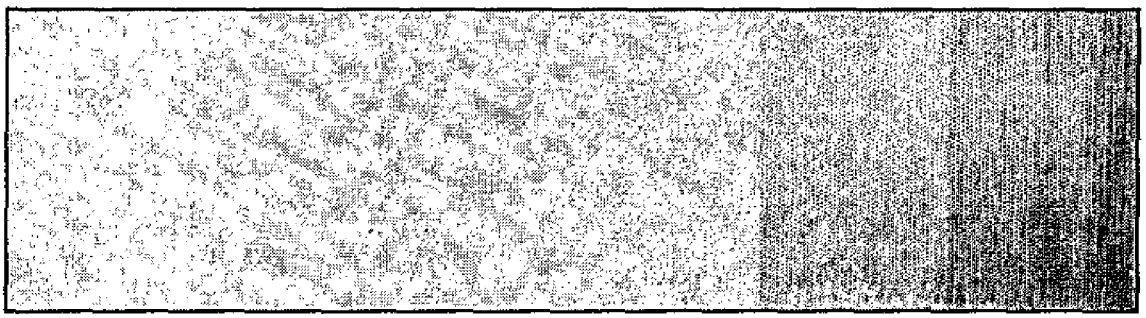

With reference to FIG. 1, in step (a) a first layer of coloured cosmetic product in the melted state is poured within a first containment perimeter being laid on a plane in this embodiment. The cosmetic is advantageously metered such as to fill said first containment perimeter to the rim thereof.

In step (b) a second containment perimeter is placed on the first containment perimeter and, after the poured cosmetic product of step (a) has solidified, a second cosmetic product of a different colour from the previous one is poured on top thereof.

In step (b') the operation described in step (b) is repeated twice.

In step (c), after all the layers have solidified, the containment perimeters are removed, thereby the multicoloured solid block consisting of the various layers of the poured cosmetic products are released.

Finally, in step (d), said block is cut into sections incident to the layers of poured cosmetic products.

FIG. 1 also shows two further processing steps, particularly the multicoloured or "dégradé" sections being inserted in the base and the finished product being pressed.

The different cosmetic products poured within the containment perimeter have at least two different colours, such that a multilayered, multicoloured or "dégradé" block is obtained by superimposing several castings of cosmetic products of different colours.

According to an embodiment of the present invention, a shaded effect (also called "dégradé") can be obtained by progressively intensifying the nuance of a selected colour throughout the various layers. Thus, the resulting multicoloured block will be formed by coloured layers of the same colour in various shades.

According to an alternative embodiment, the layers can be of very different colours, such as to obtain a multicoloured cosmetic consisting of portions of variously coloured cosmetic products that are arranged to form any colour effect.

The amount of the cosmetic product to be poured per each layer will be selected by those skilled in the art as a function of the size and thickness desired for the layer. These layers are not necessarily required to have the same thickness, but layers of different thicknesses can be freely alternated according to the thickness of each layer of poured cosmetic product one desires to obtain for the finished product.

In other words, the variously coloured cosmetic products being poured one on top of the other according to the process of the invention will be quantitatively equal to or different from each other, thereby generating polychrome or "dégrade" layers with the same or different thickness.

In step (c) the containment perimeter is removed from the multilayered, multicoloured block, either manually or by means of a machine suitable to the purpose, thereby releasing said solid block. The solid block thus obtained, after it has been optionally sized such that the sections thereof can be adapted within a final container, is cut according to planes incident to the superimposed multicoloured layers such as to form multicoloured sections that are the finished product and advantageously placed in suitable bases and optionally packaged for distribution.

The packaging of the finished product resulting from the process of the invention can take place individually, or said product can be packaged together with other cosmetic products.

Sectioning can be carried out by hand, or advantageously by means of suitable machines.

Alternatively, the sections of the solid block being obtained at the end of step (d) can be sized.

The multicoloured or "dégradé" sections thus obtained can then take the most varied shapes, such as round, oval, square, rectangular, star-like, flower-like, etc.

If desired, the multicoloured or "dégrade" sections can be pressed by means of conventional machines before they are finally packaged. By this operation, signs, figures or marks can be further printed on the surface of the finished products.

If desired, the multicoloured or "dégradé" sections can be processed by suitable machines, in order to engrave signs, figures or marks thereon or obtain particular three-dimensional shapes, either the same or different, in the various colours resulting from the poured layers. Thus, with the process of the invention, multicoloured poured cosmetic products consisting of a plurality of adjacent cosmetic products of different colours can be obtained, thereby avoiding the risk that differently coloured products may be admixed as is characteristic in the prior art, while avoiding the use of separate compartments. Accordingly, it is understood that the process of the invention considerably improves and simplifies the known processes for making multicoloured poured cosmetic products in solid form, in addition to reducing the costs associated thereto.

The invention claimed is:

1. A process for preparing a multicoloured poured cosmetic product, comprising the steps of:
    a) arranging a first layer of cosmetic product by pouring a preset amount of a first melted coloured cosmetic product on a plane, within a square or rectangular containment perimeter;
    after the layer of the preceding step has solidified, pouring directly over the solidified layer to spread out horizontally thereon a preset amount of a second cosmetic product of a different colour from the first one within the square or rectangular containment perimeter;
    b') optionally repeating step (b) one or more times in order to add layers of cosmetic products of different colours;
    c) removing the containment perimeter, thereby obtaining a multicoloured or "dégradé", multilayered block;
    d) sectioning, according to cutting planes incident to the layers of coloured cosmetic products, the multicoloured or "dégradé" multilayered block in order to obtain multicoloured or "dégradé" sections of the same.

2. The process according to claim 1, wherein said multicoloured poured cosmetic product is a lipstick, a gloss or a cosmetic for the eye contour area.

3. The process according to claim 1, wherein said containment perimeter consists of a single hollow cylindrical structure of a sufficient height to contain all the layers of poured products.

4. The process according to claim 1, wherein said containment perimeter consists of two or more hollow cylindrical elements, each having the same height as a layer of poured product to be sequentially superimposed upon steps (b) and (b').

5. The process according to claim 1, wherein said containment perimeter is square or rectangular.

6. The process according to claim 1, said containment perimeter is made of metal, glass, plastic or silicone material.

7. The process according to claim 1, wherein said poured layers of steps (a), (b) and (b') have the same thickness.

8. The process according to claim 1, wherein said poured layers of steps (a), (b) and (b') have a different thickness.

9. The process according to claim 1, wherein the multilayered block is sized either before or after the sectioning step (d).

10. The process according to claim 1, wherein said multicoloured poured cosmetic product is inserted in a suitable bottom base and optionally further packaged.

11. The process according to claim 10, wherein said multicoloured poured cosmetic product is subjected to pressing before being optionally packaged.

12. The process according to claim 1, wherein signs, figures or marks are printed on said sectioned poured cosmetic product by means of pressing.

13. The process according to claim 1, wherein the sections are further processed in order to engrave signs, figures or marks thereon, or obtain particular three-dimensional shapes.

* * * * *